US 8,128,981 B2

(12) United States Patent
Popovich et al.

(10) Patent No.: US 8,128,981 B2
(45) Date of Patent: Mar. 6, 2012

(54) BIOSENSOR MANUFACTURING METHOD

(75) Inventors: Natasha Popovich, Pompano Beach, FL (US); Dennis Slomski, Wellington, FL (US); David Deng, Weston, FL (US)

(73) Assignee: Nipro Diagnostics, Inc., Fort Lauderdale, FL (US)

( * ) Notice: Subject to any disclaimer, the term of this patent is extended or adjusted under 35 U.S.C. 154(b) by 1277 days.

(21) Appl. No.: 11/783,568

(22) Filed: Apr. 10, 2007

(65) Prior Publication Data

US 2007/0286772 A1  Dec. 13, 2007

Related U.S. Application Data

(60) Provisional application No. 60/790,773, filed on Apr. 11, 2006, provisional application No. 60/878,454, filed on Jan. 4, 2007.

(51) Int. Cl.
*G01N 1/28* (2006.01)
(52) U.S. Cl. .... 427/2.11; 436/514; 438/494; 205/777.5; 427/58; 427/96.1; 427/289; 427/292
(58) Field of Classification Search ............... 436/514; 438/393; 205/777.5; 427/2.11
See application file for complete search history.

(56) References Cited

U.S. PATENT DOCUMENTS

| 6,287,451 | B1 * | 9/2001 | Winarta et al. | 205/777.5 |
| 6,764,914 | B2 * | 7/2004 | See et al. | 438/393 |
| 2003/0116447 | A1 | 6/2003 | Surridge et al. | |
| 2004/0182703 | A1 | 9/2004 | Bell et al. | |
| 2005/0019953 | A1 * | 1/2005 | Groll | 436/514 |

FOREIGN PATENT DOCUMENTS

| EP | 1 302 545 A2 | 4/2003 |
| WO | WO 01/25775 A1 | 4/2001 |
| WO | WO 2005/066616 A2 | 7/2005 |

* cited by examiner

*Primary Examiner* — Dah-Wei Yuan
*Assistant Examiner* — Andrew Bowman
(74) *Attorney, Agent, or Firm* — Finnegan, Henderson, Farabow, Garrett & Dunner, LLP

(57) ABSTRACT

A biosensor having a first conductive component is described, wherein the first conductive component includes at least one boundary formed by a first processing technique and at least one boundary formed by a second processing technique not the same as the first processing technique. The biosensor can also have a second conductive component including at least one boundary formed by the first processing technique and at least one boundary formed by a third processing technique not the same as the first processing technique. Further, the biosensor has a third conductive component including at least one boundary formed by the second processing technique and at least one boundary formed by the third processing technique not the same as the second processing technique.

37 Claims, 7 Drawing Sheets

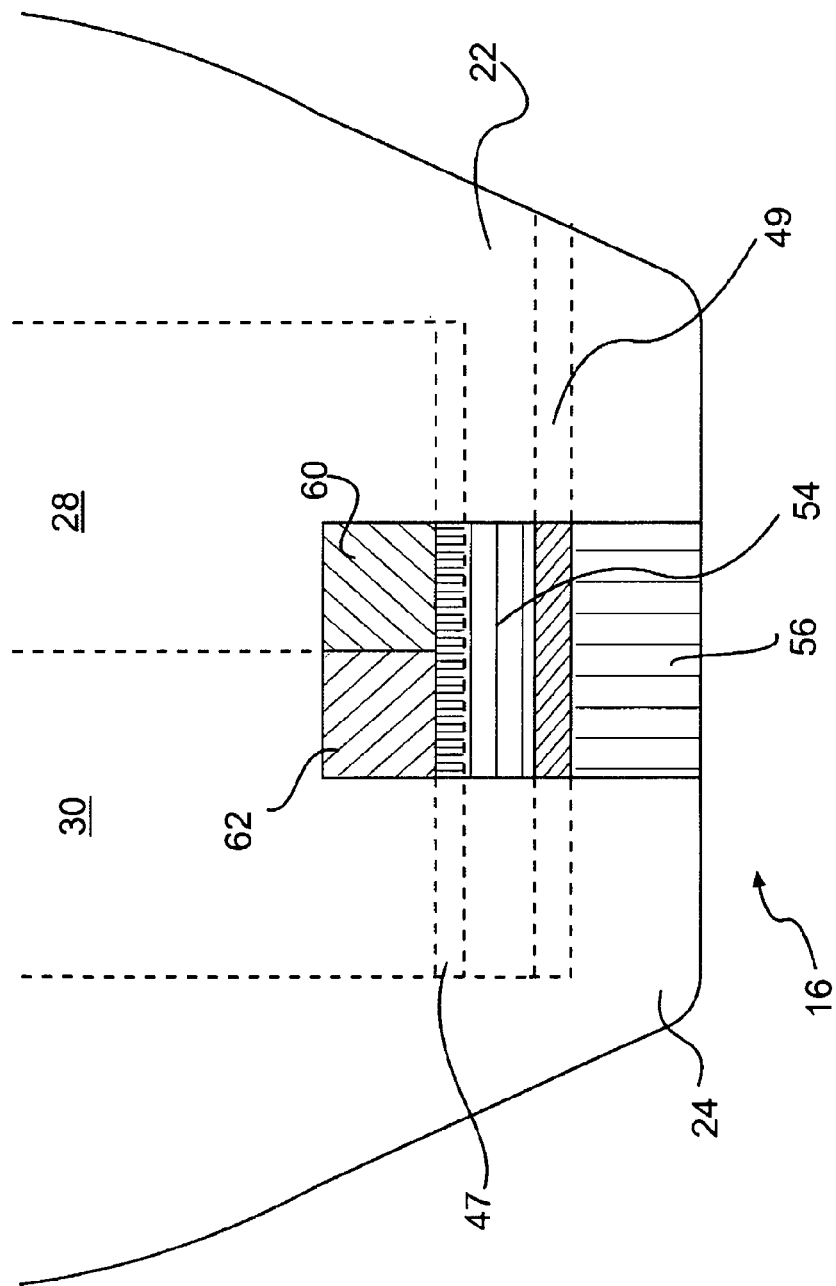

BIOSENSOR MANUFACTURING METHOD

DESCRIPTION OF THE INVENTION

This application claims priority to U.S. Provisional Application 60/790,773, filed on Apr. 11, 2006, and U.S. Provisional Application 60/878,454 filed on Jan. 4, 2007, both of which are herein incorporated by reference.

TECHNICAL FIELD

The present invention relates to electrochemical biosensors, and more particularly, to methods and systems for manufacturing biosensors.

BACKGROUND

Many people require daily monitoring of their blood glucose levels. A number of available systems allow people to conveniently monitor their blood glucose levels. Such systems typically include a disposable test strip to which the user applies a blood sample, and a meter that determines the blood glucose level.

Among the various technologies available for measuring blood glucose levels, electrochemical technologies are desirable at least in part because small volumes of blood sample can be used. In electrochemical-based systems, the test strip typically includes electrodes and a sample chamber that contains chemical constituents, such as a glucose enzyme and an electron mediator. When the user applies a blood sample to the test strip, blood is drawn into the sample chamber, and chemical constituents react with the glucose present in the blood. In amperometric electrochemical systems, the instrument applies a voltage to the electrodes to cause a redox reaction. The meter initiates one or more current measurements and calculates the glucose level based on at least one of the current measurements.

There remains a continual need to develop accurate measurements of blood glucose levels, which can help maintain the long-term health of many users. Exemplary areas of development include enhanced reliability, ease-of-use, and robust tolerance of poor user technique in the design of meters and test strips. However, as sample sizes become smaller, the dimensions of the sample chamber and electrodes in the test strip must also become smaller. This, in turn, can render the test systems more sensitive to manufacturing process and component variations, environmental factors, user technique shortcomings, damage from handling, etc. Accordingly, there is a continuing need for reliable low-volume biosensor test-strips, and also for low cost, high manufacturing volume, efficient biosensor test strip manufacturing processes.

Several methods for manufacturing biosensors have been proposed. One such method is described in U.S. Pat. No. 6,875,327 to Mivazaki et al. Miyazaki et al. describe a biosensor manufacturing process whereby a conductive layer is formed on a support.

Electrodes are formed using a laser to form multiple "slits" in the conductive layer, electrically separating the working, counter and detecting electrodes. Following electrode formation, chemical reagents are selectively applied to the conductive layer.

Although the electrode design described by Miyazaki et al. can provide a functional biosensor, the manufacturing process can be improved. Specifically, the manufacturing process can be inefficient, time consuming, or unsuitable to form one or more biosensors described in the present disclosure.

The present disclosure is directed to a manufacturing method designed to overcome one or more of the limitations in the prior art.

SUMMARY OF THE INVENTION

The present invention includes a biosensor having a first conductive component including at least one boundary formed by a first processing technique and at least one boundary formed by a second processing technique not the same as the first processing technique. The biosensor can also have a second conductive component including at least one boundary formed by the first processing technique and at least one boundary formed by a third processing technique not the same as the first processing technique. Further, the biosensor has a third conductive component including at least one boundary formed by the second processing technique and at least one boundary formed by the third processing technique not the same as the second processing technique.

Another embodiment of the invention is directed to a method of manufacturing test strips. The method can include forming a reel containing a conductive layer and a base layer. The method includes forming a first conductive component, wherein the first conductive component includes at least one boundary formed by a first processing technique and at least one boundary formed by a second processing technique not the same as the first processing technique. A second conductive component can be formed, wherein the second conductive component includes at least one boundary formed by the first processing technique and at least one boundary formed by a third processing technique not the same as the first processing technique. The method also includes forming a third conductive component, wherein the third conductive component includes at least one boundary formed by the second processing technique and at least one boundary formed by the third processing technique not the same as the second processing technique.

Another embodiment of the invention is directed to a method of manufacturing test strips. The method can include forming a reel containing a conductive layer and a base layer, and forming a first kerf in the conductive layer, wherein the first kerf can be formed using a first laser ablation process. The method can also include forming a second kerf in the conductive layer, wherein the second kerf can be formed using a second laser ablation process that is not the same as the first laser ablation process, and separating one or more test strips from the reel using a singulation process.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specific embodiments presented herein:

FIG. 3 is a magnified top plan view of the proximal end of a test strip according to an illustrative embodiment of the invention.

DETAILED DESCRIPTION

In accordance with an illustrative embodiment, a biosensor design, manufacturing method and method for measuring a fluid constituent is described. Many industries have a commercial need to monitor the concentration of particular constituents in a fluid. Oil refining, winemaking, and dairy are examples of industries where fluid testing is routine. In the health care field, people such as diabetics, for example, have a need to monitor a particular constituent within their bodily fluids using a biosensor. A number of systems are available that allow people to test a body fluid, such as, blood, urine, or saliva, to conveniently monitor the level of a particular fluid constituent, such as, for example, cholesterol, proteins, and glucose.

A biosensor may include a test strip, which can be disposable, that may facilitate the detection of a particular constituent of a fluid. The test strip can include a proximal end, a distal end and at least one electrode. The proximal end of the test strip may include a sample chamber for receiving a fluid to be tested. The sample chamber can be dimensioned and arranged to draw-in and hold a blood sample in the sample chamber to contact the electrodes by capillary action. The distal end of the test strip may be configured to operatively connect the test strip to a meter that may determine the concentration of the fluid constituent. The test strip can have, near its distal end, a plurality of electrical contacts that provide operative connection between the electrodes and the meter. The ends of the test strip can further include improved visual and/or tactile distinguishable section, such as, for example, a taper, in order to make it easier for the user to operatively connect the test strip to the meter or apply a fluid to the sample chamber.

The at least one electrode may include a working electrode, a counter electrode, and a fill-detect electrode. A diffusion barrier can be disposed between any adjacent electrodes, such as, for example, the working electrode and counter electrode. A reagent layer can be disposed in the sample chamber and may cover at least a portion of the working electrode, which can also be disposed at least partially in the sample chamber. The reagent layer can include, for example, an enzyme, such as glucose oxidase or glucose dehydrogenase, and a mediator, such as potassium ferricyanide or ruthenium hexamine, to facilitate the detection of glucose in blood. It is contemplated that other reagents and/or other mediators can be used to facilitate detection of glucose and other constituents in blood and other fluids.

Test Strip Configuration

Figure 1A:
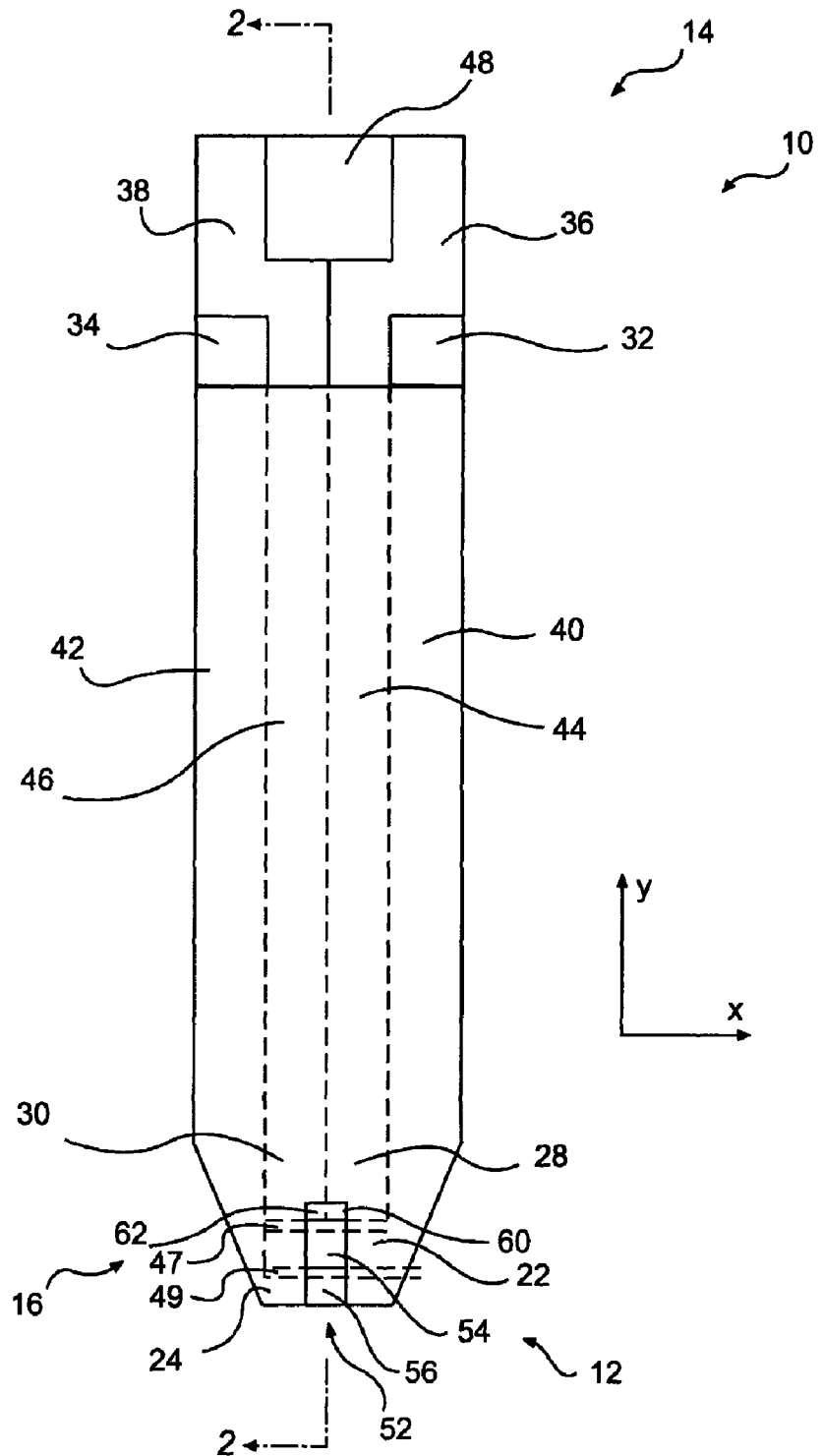
FIG. 1A is a top plan view of a test strip according to an illustrative embodiment of the invention.
Figure 2:
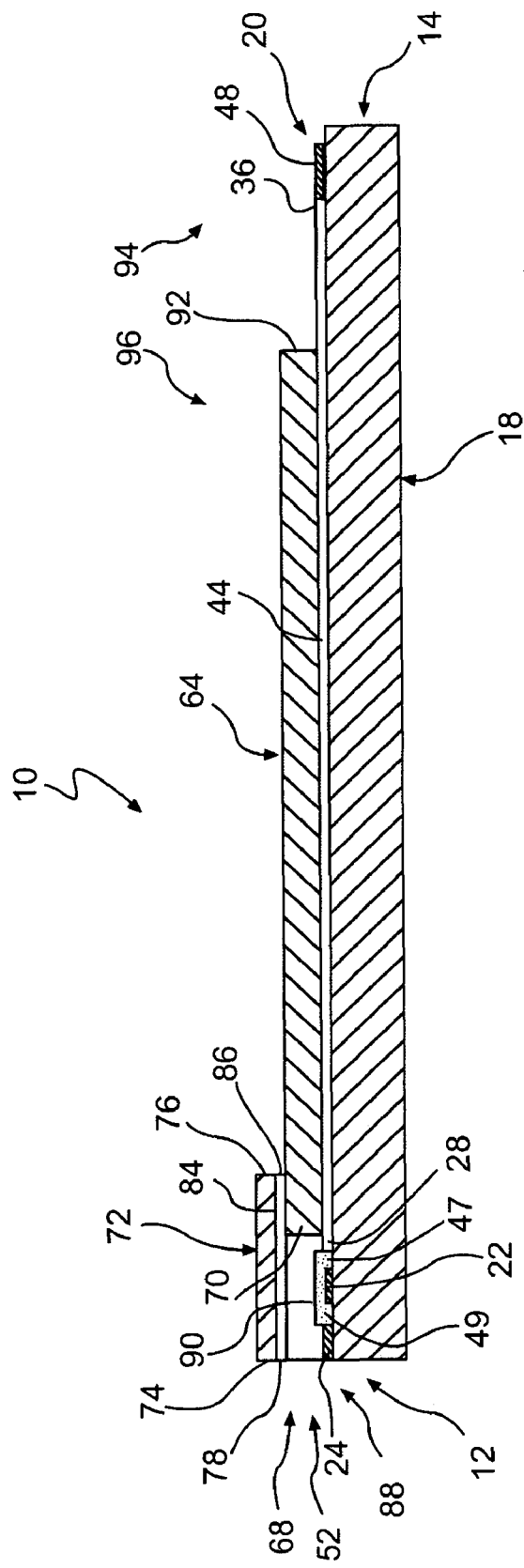
FIG. 2 is a cross-sectional view of the test strip of FIG. 1A, taken along line 2-2.

With reference to the drawings, FIGS. 1A and 2 show a test strip 10, in accordance with an illustrative embodiment of the present invention. Test strip 10 can take the form of a substantially flat strip that extends from a proximal end 12 to a distal end 14. In one embodiment, the proximal end 12 of test strip 10 can be narrower than distal end 14 to provide facile visual recognition of distal end 14. For example, test strip 10 can include a tapered section 16, in which the full width of test strip 10 tapers down to proximal end 12, making proximal end 12 narrower than distal end 14. If, for example, a blood sample is applied to an opening in proximal end 12 of test strip 10, providing tapered section 16 and making proximal end 12 narrower than distal end 14, can, in certain embodiments, assist the user in locating the opening where the blood sample is to be applied. Further or alternatively, other visual means, such as indicia, notches, contours, textures, or the like can be used.

Test strip 10 is depicted in FIGS. 1A and 2 as including a plurality of conductive components, such as, for example, electrodes. A conductive component can include any structure configured to at least partially conduct an electrical signal. In some embodiments, a conductive component can extend substantially along the length of test strip 10 to provide an electrical contact near distal end 14 and a conductive region electrically connecting the region of the electrode near proximal end 12 to the electrical contact. In the illustrative embodiment of FIGS. 1A and 2, the plurality of electrodes includes a working electrode 22, a counter electrode 24, a fill-detect anode 28, and a fill-detect cathode 30. Correspondingly, the electrical contacts can include a working electrode contact 32, a counter electrode contact 34, a fill-detect anode contact 36, and a fill-detect cathode contact 38 positioned at distal end 14. The conductive regions can include a working electrode conductive region 40, electrically connecting the proximal end of working electrode 22 to working electrode contact 32, a counter electrode conductive region 42, electrically connecting the proximal end of counter electrode 24 to counter electrode contact 34, a fill-detect anode conductive region 44 electrically connecting the proximal end of fill-detect anode 28 to fill-detect contact 36, and a fill-detect cathode conductive region 46 electrically connecting the proximal end of fill-detect cathode 30 to fill-detect cathode contact 38.

In one embodiment, at least one electrode is partially housed within the sample chamber to allow contact with the fluid to be tested. For example, FIGS. 1A and 2 depict test strip 10 as including slot 52, forming a portion of a sample chamber 88 at proximal end 12. Slot 52 can define an exposed portion 54 of working electrode 22, an exposed portion 56 of counter electrode 24, an exposed portion 60 of fill-detect anode 28, and an exposed portion 62 of fill-detect cathode 30. Further, the illustrative embodiment is depicted including an optional auto-on conductor 48 disposed near distal end 14 to allow the meter to determine that a test strip is operatively connected to the meter.

Figure 1B:
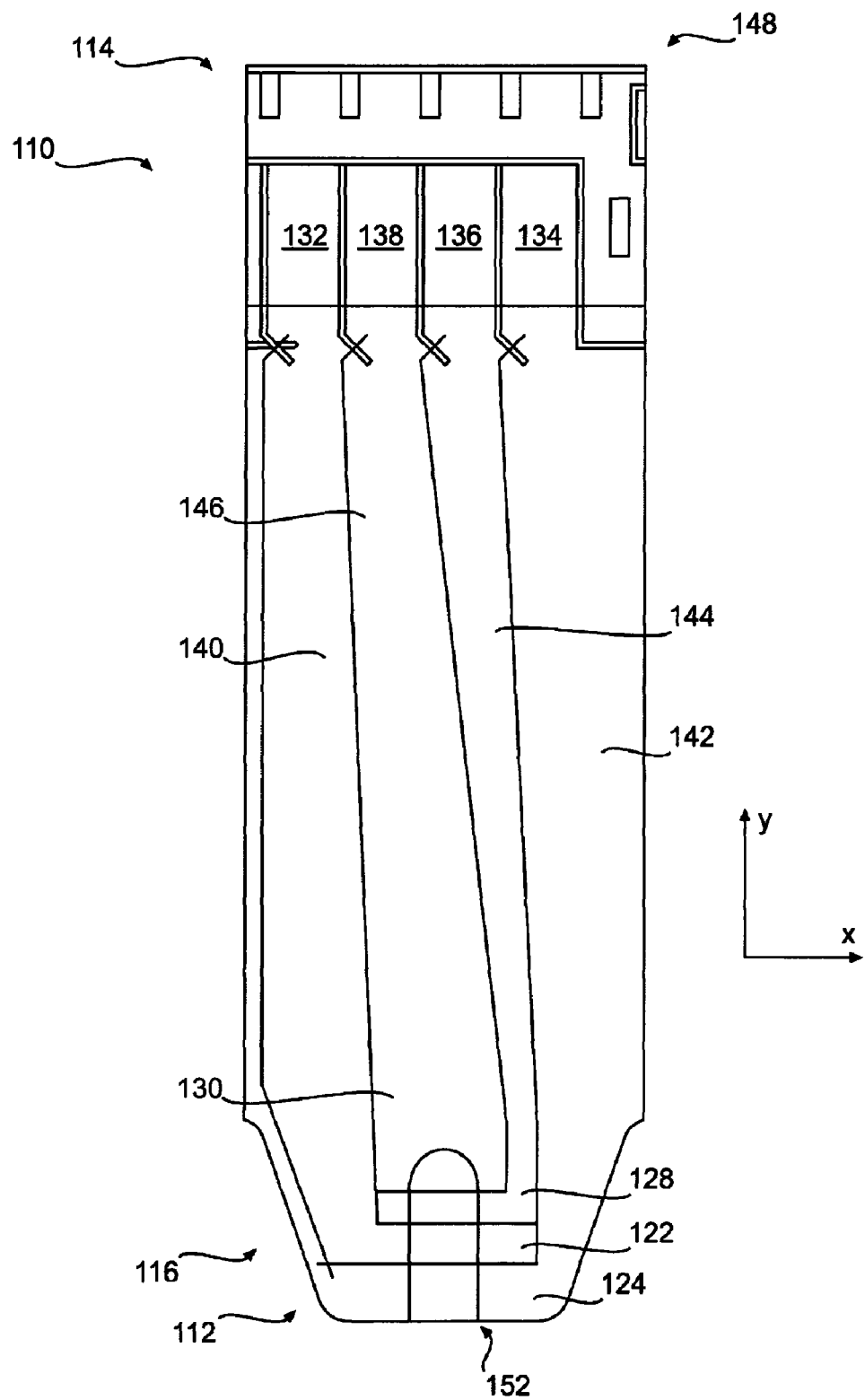
FIG. 1B is a top plan view of a test strip according to another illustrative embodiment of the invention.

FIG. 1B is a top plan view of test strip 110 according to another illustrative embodiment of the invention. As shown, test strip 110 includes a different electrode configuration, and a plurality of encoded electrical contacts 148 disposed near a distal end 114. Test strip 110 can take the form of a substantially flat strip that extends from a proximal end 112 to distal end 114, wherein the proximal end 112 of test strip 110 can be narrower than distal end 114 to provide facile visual recognition of distal end 14. For example, test strip 110 can include a tapered section 116.

Test strip 110 depicted in FIG. 1B can include a plurality of electrodes, such as, for example, a working electrode 122, a counter electrode 124, and fill-detect electrodes 128, 130. Correspondingly, the electrical contacts can include a working electrode contact 132, a counter electrode contact 134, and fill-detect electrode contacts 136, 138 positioned at distal end 114. The conductive regions can include a working electrode conductive region 140, electrically connecting the proximal end of working electrode 122 to working electrode contact 132, a counter electrode conductive region 142, electrically connecting the proximal end of counter electrode 124 to counter electrode contact 134, and fill-detect conductive regions 144, 146 electrically connecting fill-detect electrodes 128, 130 to fill-detect contacts 136, 138. Test strip 110 can also include a slot 152 configured to receive a fluid sample. In addition, test strip 110 can include one or more diffusion barriers (not shown), as described below.

In some embodiments, test strip 110 can include one or more encoded electrical contacts 148 configured to encode a readable code, wherein the readable code can include test strip information, calibration information, or any other suitable data. In addition, encoded electrical contacts 148 can be resistant to scratching or abrasion. Specifically, test strip 110 can include encoded electrical contacts 148 formed of two or more layers of conductive and/or semi-conductive material (not shown). Further information relating to encoded electrical contacts 49 encoding and abrasion resistance are described in co-owned U.S. patent application Ser. No. 11/458,298, which is incorporated by reference herein in its entirety.

FIG. 3 shows a top plan view of a test strip according to an illustrative embodiment. As shown in FIG. 3, a diffusion barrier 47 may be formed between working electrode 22 and fill-detect anode 28 and fill-detect cathode 30. Diffusion barrier 47 can electrically separate exposed portion 54 of working electrode 22 and exposed portion 60 of fill-detect anode 28 and exposed portion 62 of fill-detect cathode 30. In some embodiments, test strip 10 may also include a diffusion barrier 49 formed between working electrode 22 and counter electrode 24. Diffusion barrier 49 can electrically separate exposed portion 54 of working electrode 22 and exposed portion 56 of counter electrode 24. In other embodiments, test strip 10 may include one or more diffusion barriers positioned between any adjacent electrodes.

Diffusion barriers may be configured to improve the accuracy of determining constituent concentration by reducing the migration of electrochemically active components. For example, oxidized or reduced species formed by a redox reaction in the detection of glucose may migrate between working electrode 22 and counter electrode 24. This migration may generate spurious current, reducing the accuracy of constituent concentration determination. The width of diffusion barrier 49 may provide sufficient distance to reduce the effects of migration of electrochemically active components between exposed portion 54 of working electrode 22 and exposed portion 56 of counter electrode 24.

The equation for determining the diffusion distance of an electroactive chemical component is given by:

$$d=\sqrt{2Dt}$$

where d is the diffusion distance, D is the diffusion coefficient, and t is time. For example, the diffusion coefficient is ~7.6×10$^{-6}$ cm$^2$/sec for potassium ferricyanide and ~8.8×10$^{-6}$ cm$^2$/sec for ruthenium hexamine. During an illustrative reaction time of 5 seconds, charged potassium ferricyanide may migrate 87 micro-meters and charged ruthenium hexamine may migrate 93 micro-meters. It has been found that the current caused by migrating charged components may be reduced by separating working electrode 22 and counter electrode 24 by a distance approximately equal to or greater than the diffusion distance, such as, for example, approximately 100 micro-meters for a biosensor using potassium ferricyanide or ruthenium hexamine. According to the illustrative embodiment, diffusion barrier 49 may separate working electrode 22 and counter electrode 24 by at least approximately 100 micro-meters.

In some embodiments, the diffusion distance for a given mediator is dependent upon the reaction time. For example, shorter reaction times decrease the diffusion distance. Subsequently, the width of diffusion barrier can be decreased. Longer reaction times increase diffusion distance, and subsequently, the width of diffusion barrier can increase. It is also contemplated that the diffusion distance may vary depending upon other factors related to the design and/or function of test strip 10, such as, for example, geometry, surface energy, and environmental factors.

As shown in FIG. 2, test strip 10 can have a generally layered construction.

Working upwardly from the bottom layer, test strip 10 can include a base layer 18 that can substantially extend along the entire length or define the length of test strip 10. Base layer 18 can be formed from an electrically insulating material and can have a thickness sufficient to provide structural support to test strip 10.

According to the illustrative embodiment of FIG. 2, a conductive layer 20 may be disposed on at least a portion of base layer 18. Conductive layer 20 can comprise a plurality of electrodes. In the illustrative embodiment, the plurality of electrodes includes a working electrode 22, a counter electrode 24, a fill-detect anode 28, and a fill-detect cathode 30. Further, the illustrative embodiment is depicted with conductive layer 20 including an auto-on conductor 48 disposed on base layer 18 near distal end 14. In addition, diffusion barrier 49 may be a non-conductive region formed in conductive layer 20. It is contemplated that diffusion barrier 49 may be formed by at least partially ablating conductive layer 20 between working electrode 22 and counter electrode 24.

The next layer of the illustrative test strip 10 is a dielectric spacer layer 64 disposed on conductive layer 20. Dielectric spacer layer 64 may be composed of an electrically insulating material, such as polyester. Dielectric spacer layer 64 can cover portions of working electrode 22, counter electrode 24, fill-detect anode 28, fill-detect cathode 30, and conductive regions 40-46, but in the illustrative embodiment of FIG. 2 does not cover electrical contacts 32-38, and/or auto-on conductor 48. For example, dielectric spacer layer 64 can cover a substantial portion of conductive layer 20 thereon, from a line proximal of contacts 32 and 34 to proximal end 12, except for slot 52 extending from proximal end 12.

A cover 72, having a proximal end 74 and a distal end 76, is shown in FIG. 2 as being disposed at proximal end 12 and configured to cover slot 52 and partially form sample chamber 88. Cover 72 can be attached to dielectric spacer layer 64 via an adhesive layer 78. Adhesive layer 78 can include a polyacrylic or other adhesive and can consist of sections disposed on cover 72 on opposite sides of slot 52. A break 84 in adhesive layer 78 extends from distal end 70 of slot 52 to an opening 86. Cover 72 can be disposed on spacer layer 64 such that proximal end 74 of cover 72 may be aligned with proximal end 12 and distal end 76 of cover 72 may be aligned with opening 86, thereby covering slot 52 and break 84. Further, cover 72 can be composed of an electrically insulating material, such as polyester. Cover 72 can also be transparent.

Slot 52, together with base layer 18 and cover 72, can define sample chamber 88 in test strip 10 for receiving a fluid sample, such as a blood sample, for measurement in the illustrative embodiment. A proximal end 68 of slot 52 can define a first opening in sample chamber 88, through which the fluid sample is introduced. At distal end 70 of slot 52, break 84 can define a second opening in sample chamber 88, for venting sample chamber 88 as sample enters sample chamber 88. Slot 52 may be dimensioned such that a blood sample applied to its proximal end 68 is drawn into and held in sample chamber 88 by capillary action, with break 84 venting sample chamber 88 through opening 86, as the blood sample enters. In some embodiments, cover 72 can include one or more holes, or vents (not shown), configured to permit fluid flow into chamber 88. Moreover, slot 52 can be dimensioned so that the volume of blood sample that enters sample chamber 88 by capillary action is about 1 micro-liter or less.

A reagent layer 90 may be disposed in sample chamber 88. In the illustrative embodiment, reagent layer 90 contacts exposed portion 54 of working electrode 22. It is also contemplated that reagent layer 90 may or may not contact diffusion barrier 49 and/or exposed portion 56 of counter electrode 24. Reagent layer 90 may include chemical components to enable the level of glucose or other analyte in the fluid, such as a blood sample, to be determined electro-chemically. For example, reagent layer 90 can include an enzyme specific for glucose, such as glucose dehydrogenase or glucose oxidase, and a mediator, such as potassium ferricyanide or ruthenium hexamine. Reagent layer 90 can also include other components, such as buffering materials (e.g., potassium phosphate), polymeric binders (e.g., hydroxypropyl-methyl-cellulose, sodium alginate, microcrystalline cellulose, polyethylene oxide, hydroxyethylcellulose, and/or polyvinyl alcohol), and surfactants (e.g., Triton X-100 or Surfynol 485).

Chemical components of reagent layer 90 can react with glucose in the blood sample in the following way. The glucose oxidase initiates a reaction that oxidizes the glucose to gluconic acid and reduces the ferricyanide to ferrocyanide. When an appropriate voltage is applied to working electrode 22, relative to counter electrode 24, the ferrocyanide is oxidized to ferricyanide, thereby generating a current that is related to the glucose concentration in the blood sample.

In the determination of glucose concentration in a blood sample, diffusion barrier 49 may improve the accuracy of the determination by reducing the migration of one or more components of reagent layer 90. A component charged by oxidation or reduction, such as, for example, ruthenium hexamine, may migrate between working electrode 22 and counter electrode 24. The migration or "shuttling" of the charged components may generate spurious current, reducing the accuracy of glucose concentration determination. The width of diffusion barrier 49 is designed to provide sufficient distance to limit the migration of charged constituents between exposed portion 54 of working electrode 22 and exposed portion 56 of counter electrode 24.

As depicted in FIG. 2, the position and dimensions of the layers of illustrative test strip 10 can result in test strip 10 having regions of different thicknesses. Of the layers above base layer 18, the thickness of spacer layer 64 may constitute a substantial thickness of test strip 10. Thus the distal end of spacer layer 64 may form a shoulder 92 in test strip 10. Shoulder 92 may delineate a thin section 94 of test strip 10 extending from shoulder 92 to distal end 14, and a thick section 96 of test strip 10 extending from shoulder 92 to proximal end 12. The elements of test strip 10 used to electrically connect it to the meter (not shown), namely, electrical contacts 32-38 and auto-on conductor 48, can all be located in thin section 94. Accordingly, the meter can be sized and configured to receive relatively thin section 94 but not relatively thick section 96. This may help the user to insert the correct end of test strip 10, i.e., distal end 14 of relatively thin section 94, and can prevent the user from inserting the wrong end, i.e., proximal end 12 of relatively thick section 96, into the meter.

Test strip 10 can be sized for easy handling. For example, test strip 10 can measure approximately 35 mm long (i.e., from proximal end 12 to distal end 14) and about 9 mm wide. According to the illustrative embodiment, base layer 18 can be a polyester material about 0.25 mm thick and dielectric spacer layer 64 can be about 0.094 mm thick and cover portions of working electrode 22. Adhesive layer 78 can include a polyacrylic or other adhesive and have a thickness of about 0.013 mm. Cover 72 can be composed of an electrically insulating material, such as polyester, and can have a thickness of about 0.095 mm. Sample chamber 88 can be dimensioned so that the volume of fluid sample is about 1 micro-liter or less. For example, slot 52 can have a length (i.e., from proximal end 12 to distal end 70) of about 3.56 mm, a width of about 1.52 mm, and a height (which can be substantially defined by the thickness of dielectric spacer layer 64) of about 0.13 mm. The dimensions of test strip 10 for suitable use can be readily determined by one of ordinary skill in the art. For example, a meter with automated test strip handling may utilize a test strip smaller than 9 mm wide.

Although FIGS. 1A, 1B and 2 show an illustrative embodiment of test strip 10, other configurations, chemical components and electrode arrangements could be used. For example, different arrangements of working electrode, counter electrode, and/or diffusion barriers can also be used. In the configuration shown in FIGS. 1A and 2, working electrode 22, counter electrode 24 and diffusion barriers 47, 49 are separated by boundaries generally aligned in the x-axis, perpendicular to the length of test strip 10 in the y-axis. Alternatively, working electrode 22, counter electrode 24 and diffusion barrier 49 can be separated by boundaries generally aligned in the y-axis, parallel to the length of test strip 10. It is also contemplated that working electrode 22, counter electrode 24 and/or diffusion barrier 49 may be aligned at any angle relative the length of test strip 10.

Manufacturing of Test Strips

Figure 4A:
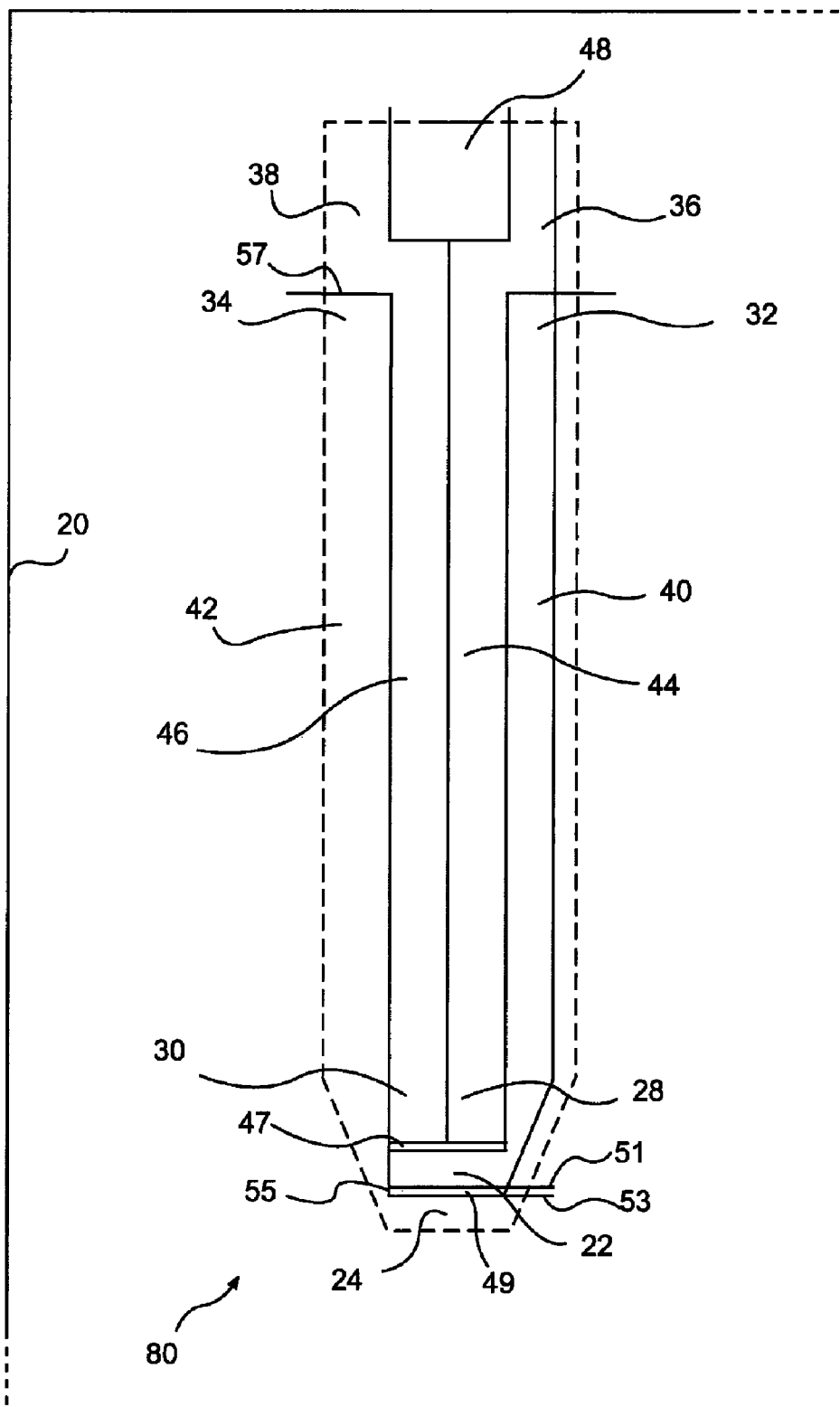
FIG. 4A is a top view of a conductive layer according to an illustrative embodiment of the invention.
Figure 4B:
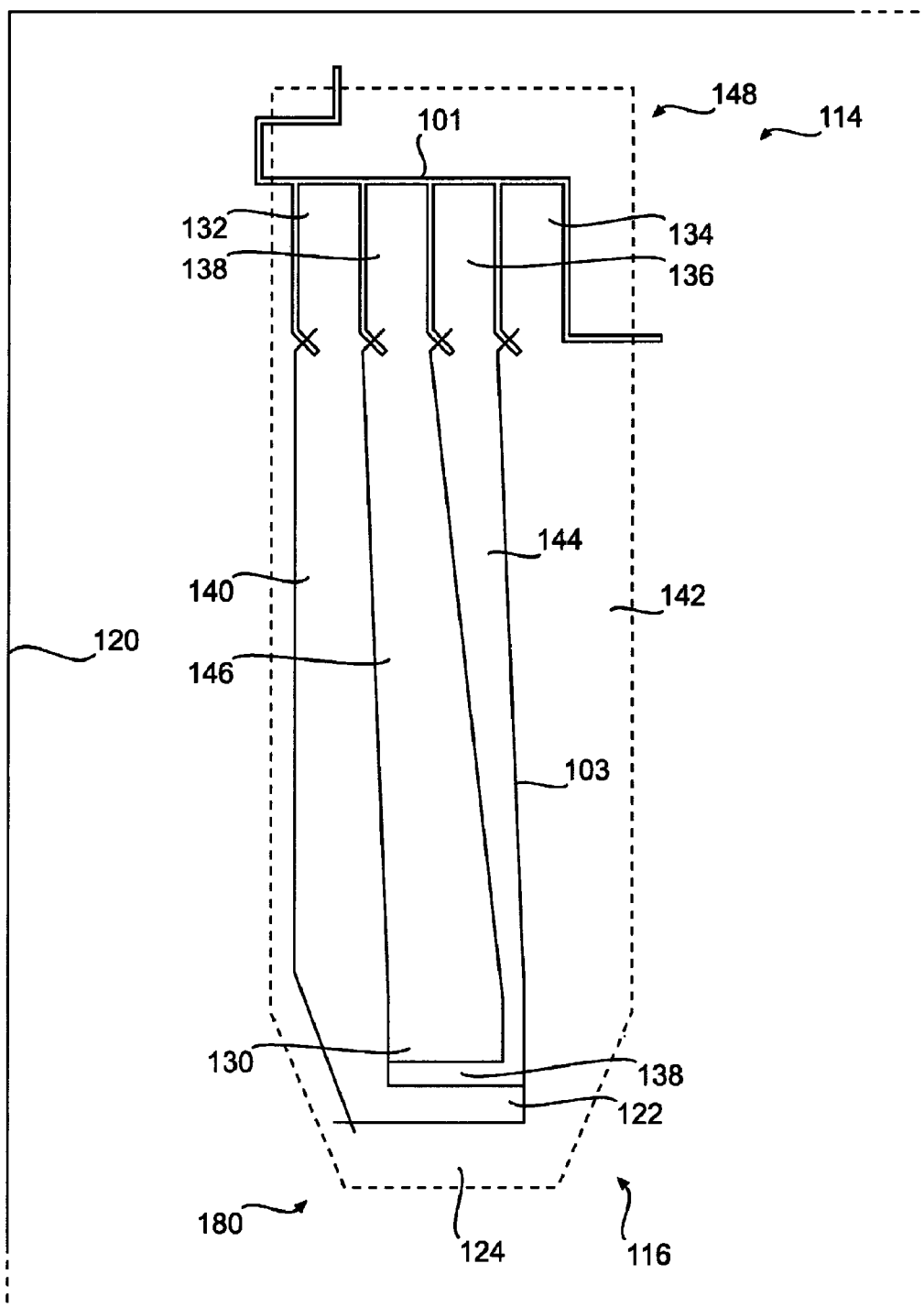
FIG. 4B is a top view of a conductive layer according to another illustrative embodiment of the invention.
Figure 5:
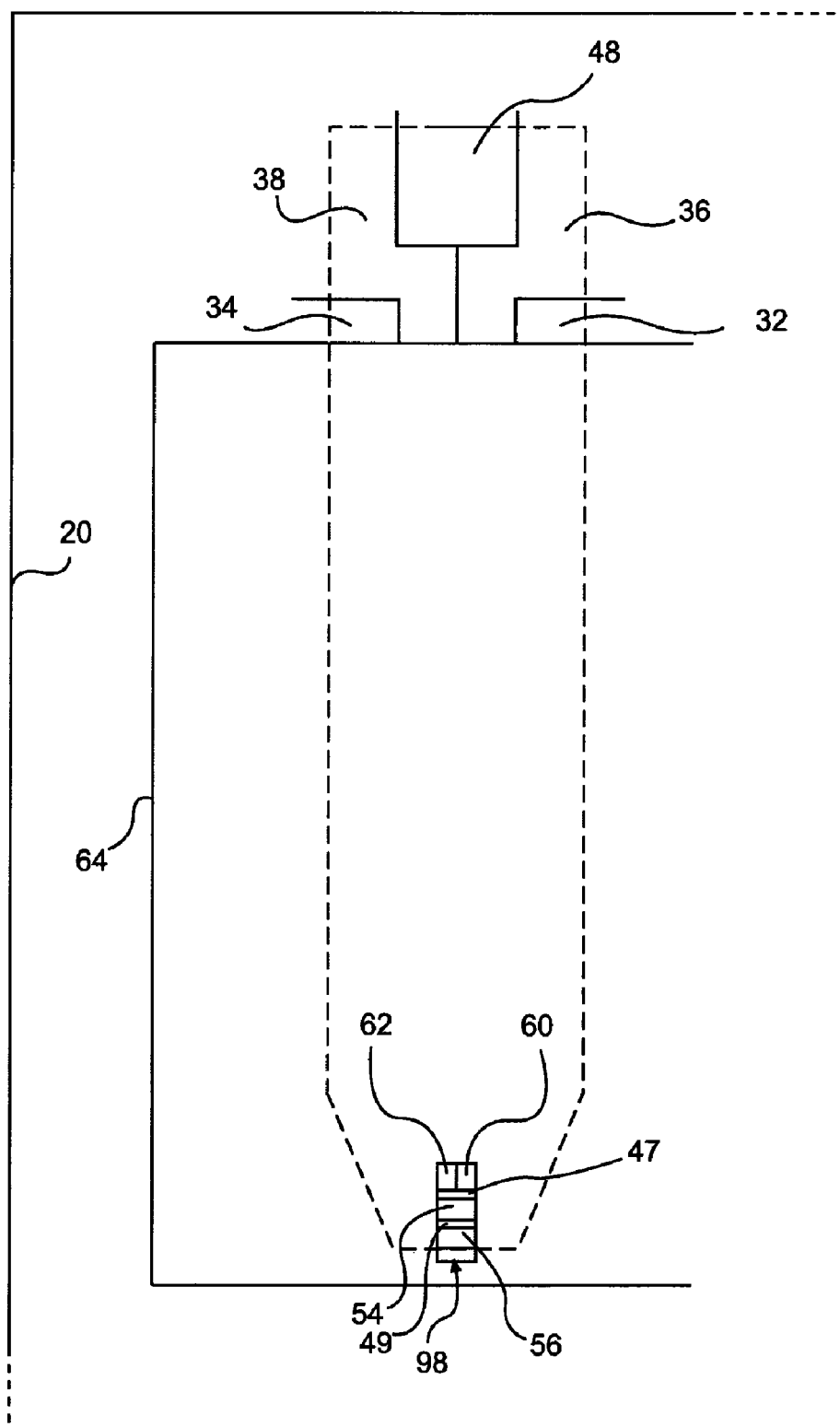
FIG. 5 is a top view of a dielectric layer according to an illustrative embodiment of the invention.

FIGS. 4A, 4B, and 5 show one test strip structure partially fabricated in order to show various steps in an illustrative method for forming the test strip. In each of FIGS. 4A, 4B, and 5, the outer shape of the test strip that would be formed in the overall manufacturing process is shown as a dotted line. Although these figures show steps for manufacturing test strip 10, as shown in FIGS. 1A, 4B, and 2, it is to be understood that similar steps can be used to manufacture test strips having other configurations of components.

Test strips 10 can be manufactured by forming a plurality of test strips 10 in an array along a reel of substrate material. The illustrative manufacturing process employs base layer 18 covered by conductive layer 20. Conductive layer 20 and base layer 18 can be in the form of a reel, such as, for example, a ribbon, web, sheet, or other similar structure. Conductive layer 20 can comprise any suitable conductive or semi-conductor material, such as gold, silver, palladium, carbon, tin oxide and others known in the art. The conductive material can be any suitable thickness and can be bonded to base layer 18 by any suitable means.

Conductive layer 20 can be formed by direct writing, sputtering, screen printing, contact printing or any suitable manufacturing method. One exemplary process is direct writing of electrodes as described in commonly-assigned, copending provisional patent application No. 60/716,120 "Biosensor with Direct Written Electrode," filed Sep. 13, 2005, the disclosure of which is hereby incorporated herein by reference in its entirety. Another exemplary process is screen printing as described in commonly-assigned, U.S. Pat. No. 6,743,635

"System and methods for blood glucose sensing," filed Nov. 1, 2002, the disclosure of which is hereby incorporated herein by reference in its entirety.

As depicted in the illustrative embodiment shown in FIG. 4A, 4B, test strip 10, 110 may include a plurality of electric components, such as, for example, electrodes 22, 122, 24, 124, 28, 128 and 30, 130 disposed in conductive layer 20, 120 and substantially extending from proximal end 12, 112 to distal end 14, 114. The electric components of test strip 10, 110 may be partially formed by forming a trace 80, 180. For example, trace 80 may be indicated by the solid lines on conductive layer 20 as shown in FIG. 4A.

Trace 80, 180 may at least partially define one or more boundaries of one or more electric components of test strip 10, 110.

In some embodiments, the electric components of the test strip may be at least partially formed by one or more processing techniques. For example, one or more boundaries of some electric components may be at least partially formed by any process used to form the conductive layer, such as, direct writing, sputtering, screen printing and contact printing. It is also contemplated that a processing technique may be used to more precisely define the boundaries of some electric components, such as, for example, laser ablation. In other embodiments, a processing technique may include lamination, etching or a physical separation processes, such as, for example, stamping and cutting.

In some embodiments, trace 80, 180 can be formed by an ablation process, such as, for example, laser ablation where laser ablation can include any device suitable for removal of the conductive layer in appropriate time and with appropriate precision and accuracy. Various types of lasers can be used for sensor fabrication, such as, for example, solid-state lasers (e.g. Nd:YAG and titanium sapphire), copper vapor lasers, diode lasers, carbon dioxide lasers and excimer lasers. Such lasers may be capable of generating a variety of wavelengths in the ultraviolet, visible and infrared regions. For example, excimer laser provides wavelength of about 248 nm, a fundamental Nd:YAG laser gives about 1064 nm, a frequency tripled Nd:YAG wavelength is about 355 nm and a Ti:sapphire laser is at approximately 800 nm. The power output of these lasers may vary and is usually in range about 10-100 watts. Alternatively, trace 80, 180 can be formed by laser ablation process in combination with other suitable processes known in the art.

The laser ablation process can include a laser system. The laser system can include a laser source. The laser system can further include means to form trace 80, 180 such as, for example, a focused beam, projected mask or other suitable technique. The use of a focused laser beam can include a device capable of rapid and accurate controlled movement to move the focused laser beam relative to conductive layer 20, 120. For example, a scanner such as HurryScan (ScanLabs) may be used to direct the laser beam in direct write applications. The use of a mask can involve a laser beam passing through the mask to selectively ablate specific regions of conductive layer 20, 120. A single mask can define trace 80, 180, or multiple masks may be required to form trace 80, 180. To form trace 80, 180, the laser system can move relative to conductive layer 20, 120. Specifically, the laser system, conductive layer 20, 120, or both the laser system and conductive layer 20, 120 may move to allow formation of trace 80, 180 by laser ablation.

Exemplary devices available for such ablation techniques include a laser system available from LasX Industries, White Bear Lake, Minn. and laser micro machining systems from Exitech, Ltd. (Oxford, United Kingdom).

In some embodiments, trace 80, 180 may include one or more kerfs at least partially electrically isolating adjacent electric components of test strip 10, 110. A kerf may form a linear and/or curvilinear electrically-isolating region between adjacent electric components. It is also contemplated that a kerf may include a turn of any angle, such as, for example, an orthogonal angle whereby the kerf forms an "L" shape.

A kerf of may partially electrically isolate adjacent electric components. In some embodiments, a kerf may partially electrically isolate adjacent electric components as the electric components may remain electrically connected following kerf formation. For example, as shown in FIG. 4A, counter electrode contact 34 and fill-detect cathode contact 38 may remain electrically connected following the formation of a kerf 57 partially separating the two electric components. Counter electrode contact 34 and fill-detect cathode contact 38 may subsequently be electrically isolated by a separation process as described below, whereby test strip 10 is separated from the laminate reel along the dashed line as shown in FIG. 4A.

In some embodiments, one or more laser ablation processing techniques may be used to form a trace. For example, a first laser ablation processing technique may utilize a first laser beam of a first width and a second laser ablation processing technique may utilize a second laser beam of a second width, wherein the first and second widths may be different. The first laser beam may be used to form one or more boundaries of contiguous electric components and the second laser beam may be used to form one or more diffusion barriers, and/or other electric components. In some embodiments, the width of the second laser beam may be at least as wide as the diffusion distance for the specific reagent used for test strip 10. For example, a second laser beam ~100 micro-meters wide may be used to form diffusion barrier 49 by at least partially removing material from conductive layer 20 between working electrode 22 and counter electrode 24. In addition, a second laser beam ~100 micro-meters wide may be used to form one or more boundaries of encoding electrical contacts 148, while a first laser beam ~20 micro-meters wide may be used to form one or more boundaries of working electrode 122, counter electrode 124, and/or fill-detect electrodes 128, 130.

In some embodiments, a first laser ablation processing technique may utilize a first laser beam generated by a first type of laser and a second laser ablation processing technique may utilize a second laser beam generated by a second type of laser, wherein the first and second types of lasers may be different. As previously described, various types of lasers may be used to form various kerfs in the test strip. For example, one kerf may be formed by a laser operating in the infrared spectrum while another kerf may be formed by a laser operating in the ultraviolet spectrum. As shown in FIG. 4B, a laser operating in the infrared spectrum could be used to form a kerf 101, while a laser operating in the ultraviolet spectrum could be used to form a kerf 103. In some embodiments, kerf 101 can form a boundary of one or more conductive components at distal end 114, such as, for example, electrical contacts 132, 134, 136, 138, and/or 148. In addition, kerf 103 can form a boundary of one or more conductive components at proximal end 116, such as, for example, electrodes 122, 124, 128, and/or 130.

In other embodiments, a first laser ablation processing technique may utilize a first laser beam generated at a first power and a second laser ablation processing technique may utilize a second laser beam generated a second power, wherein the first and second laser powers may be different. For example, one laser may have sufficient power to ablate material to a desired depth, while another laser may ablate material to a smaller or larger depth. Also, one laser may be of sufficient power to penetrate one or more layers of material, while another laser may be able to penetrate fewer or greater layers of material. As previously described, test strip 10, 110 can include electrical contacts formed of two or more layers of conductive and/or semi-conductive material, as described by U.S. patent application Ser. No. 11/458,298.

To illustrative by example, a first laser ablation process may be configured to ablate two or more layers of conductive and/or semi-conductive material to form kerf 101, while a second laser ablation process may be configured to ablate less material at a lower power to form kerf 103. For example, a TR Fiber laser manufactured by SPI (Southampton, UK) operating at suitable power may be used to form kerf 101. Such a manufacturing technique can permit formation of conductive components at proximal end 116 at appropriate resolution for the required electrochemical process and formation of conductive components at distal end 114 requiring higher power ablation to penetrate of multilayered material. Also, different laser ablation processes can be applied at different stages during a manufacturing process. For example, kerf 101 may be formed following deposition of one or more layers of conductive and/or semi-conductive material while kerf 103 may be formed prior to such a deposition process. Therefore, different processing techniques, such as lasers operating at different powers, different beam width, being of different type, etc., can be used to form one or more boundaries of one or more conductive components. For example, an AVIA-X laser manufactured by Coherent (Santa Clara, Calif.) can be used to form kerf 103 when operated at a first laser power, and kerf 101 when operated at a second laser power higher than the first laser power.

In some embodiments, diffusion barriers may be formed by a plurality of kerfs. For example, diffusion barrier 49 may be at least partially formed by kerfs 51, 53 and 55, where kerfs 51 and 53 may be any width less than the width of diffusion barrier 49. The width and/or trajectory of the one or more kerfs used to form diffusion barrier 49 may be sufficient to form a region electrically isolating working electrode 22 and counter electrode 24. For example, the distance between kerfs 51 and 53 can define the width of diffusion barrier 49 and thus the separation distance between working electrode 22 and counter electrode 24.

Diffusion barrier 49 may be contiguous with at least one boundary of one or more electric components, such as, for example, working electrode 22 and counter electrode 24. As shown in FIG. 4A, boundaries contiguous with diffusion barrier 49, working electrode 22, and counter electrode 24 may include the boundaries formed by kerfs 51, 53, and 55. Boundaries non-contiguous with diffusion barrier 49 may include the boundaries between counter electrode conductive region 42 and fill-detect cathode conductive region 46, fill-detect cathode conductive region 46 and fill-detect anode conductive region 44, and fill-detect anode conductive region 44 and working electrode conductive region 40.

Following the formation of electrical components of test strip 10, dielectric spacer layer 64 can be applied to conductive layer 20, as illustrated in FIG. 5. Spacer layer 64 can be applied to conductive layer 20 in a number of different ways. In an illustrative approach, spacer layer 64 is provided as a sheet or web large enough and appropriately shaped to cover multiple test strip traces 80. In this approach, the underside of spacer layer 64 can be coated with an adhesive to facilitate attachment to conductive layer 20. Portions of the upper surface of spacer layer 64 can also be coated with an adhesive in order to provide adhesive layer 78 in each of the test strips 10. Various slots can be cut, formed or punched out of spacer layer 64 to shape it before, during or after the application of spacer layer 64 to conductive layer 20. For example, as shown in FIG. 5, spacer layer 64 can have a pre-formed slot 98 for each test strip structure. Spacer layer 64 may then be positioned over conductive layer 20, as shown in FIG. 5, and laminated to conductive layer 20. When spacer layer 64 is appropriately positioned on conductive layer 20, exposed electrode portions 54-62 are accessible through slot 98. Similarly, spacer layer 64 leaves contacts 32-38 and auto-on conductor 48 exposed after lamination.

Alternatively, spacer layer 64 could be applied in other ways. For example, spacer layer 64 can be injection molded onto base layer 18. Spacer layer 64 could also be built up on base layer 18 by screen-printing successive layers of a dielectric material to an appropriate thickness, e.g., about 0.005 inches. An exemplary dielectric material comprises a mixture of silicone and acrylic compounds, such as the "Membrane Switch Composition 5018" available from E. I. DuPont de Nemours & Co., Wilmington, Del. Other materials could be used, however.

In some embodiments, one or more kerfs may be formed following application of spacer layer 64 to base layer 18. For example, spacer layer 64 may be applied to base layer 18 such that spacer layer 64 at least partially covers one or more electrical contacts 132, 134, 136, 138, and/or 148. Following application of spacer layer 64, one or more kerfs 101 can be formed by any suitable processing technique configured to remove sufficient material from spacer layer 64 and conductive layer 120, such as, for example, laser ablation using a high-energy or infrared laser. In other embodiments, kerf 101 can be formed following application of a second conductive layer or semi-conductive layer to distal end of the test strip, as described by U.S. patent application Ser. No. 11/458,298. Other processing techniques may be employed, including etching.

Reagent layer 90 can then be applied to each test strip structure after forming spacer layer 64. In an illustrative approach, reagent layer 90 is applied by micro-pipetting an aqueous composition onto exposed portion 54 of working electrode 22 and letting it dry to form reagent layer 90. It is also contemplated that reagent layer 90 may or may not contact diffusion barrier 49 and/or exposed portion 56 of counter electrode 24. An exemplary aqueous composition has a pH of about 6 and contains 2 weight % polyvinyl alcohol, 0.1 M potassium phosphate, 0.05 weight % Triton X-100, 0.15 M ruthenium hexamine, 0.7% hydroxyethylcellulose (such as NATROSOL®), and about 2500 units of glucose oxidase per mL. Alternatively, other methods, such as screen-printing, can be used to apply the composition used to form reagent layer 90. In other embodiments, reagent layer 90 can be applied before or concurrently with application of spacer layer 64.

Cover 72 can then be attached to space layer 64, where cover 72 is constructed to cover slot 52. Cover 72 can include adhesive layer 78 configured to adhere to spacer layer 64. Following attachment of cover 72, individual test strips 10 may be separated from the laminated reel. In an illustrative embodiment, the separation process may include stamping or "punching out" of individual test cards in a "singulation" process. For example, the singulation process could include laser ablation, stamping, cutting, or etching. In addition, one or more cover holes (not shown) can be formed in cover 72 to provide suitable venting of sample chamber 88. A cover hole could be formed by any suitable processing technique, such as, for example, laser ablation, stamping, cutting, or etching.

In some embodiments, the cover hole could be formed using a carbon dioxide laser or other type of laser operated at an appropriate energy.

Various embodiments of the present invention have been described above. Those skilled in the art will understand, however, that changes and modifications may be made to these embodiments without departing from the true scope and spirit of the invention, which is defined by the claims.

What is claimed is:

1. A method of manufacturing test strips, comprising:
   forming a reel containing a conductive layer and a base layer;
   forming a first conductive component, wherein the first conductive component includes at least one first boundary formed by the movement of a first processing source along the at least one first boundary and at least one second boundary formed by the movement of a second processing source along the at least one second boundary, the second processing source is not the same as the first processing source, and the at least one first boundary is not the same as the at least one second boundary;
   forming a second conductive component, wherein the second conductive component includes at least one third boundary formed by the movement of the first processing source along the at least one third boundary and at least one fourth boundary formed by a third processing source not the same as the first processing source, and the at least one third boundary is not the same as the at least one fourth boundary; and
   forming a third conductive component, wherein the third conductive component includes at least one fifth boundary formed by the movement of the second processing source along the at least one fifth boundary and at least one sixth boundary formed by the third processing source not the same as the second processing source, and the at least one fifth boundary is not the same as the at least one sixth boundary.

2. The method of claim 1, wherein the first processing source is configured to perform at least one technique selected from the group consisting of laser ablation, stamping, cutting, and etching.

3. The method of claim 1, wherein the second processing source is configured to perform at least one technique selected from the group consisting of laser ablation, stamping, cutting, and etching.

4. The method of claim 1, wherein the third processing source is configured to perform at least one technique selected from the group consisting of laser ablation, stamping, cutting, and etching.

5. The method of claim 1, wherein the first processing source includes a first laser configured to emit a first ablative beam width and the second processing source includes a second laser configured to emit a second ablative beam width, wherein the first ablative beam width and the second ablative beam width are not the same.

6. The method of claim 5, wherein the first ablative beam width is at least approximately 20 micro-meters.

7. The method of claim 5, wherein the second ablative beam width is at least approximately 100 micro-meters.

8. The method of claim 5, wherein substantially all of the conductive material between adjacent conductive components is removed and a distance between the adjacent conductive components is substantially equal to at least one of the first ablative beam width and the second ablative beam width.

9. The method of claim 1, wherein the first processing source includes a first type of laser and the second processing source includes a second type of laser, wherein the first type of laser and the second type of laser are not the same.

10. The method of claim 9, wherein the first or second type of laser is selected from the group consisting of a solid-state laser, a copper vapor laser, a diode laser, a carbon dioxide laser, and an excimer laser.

11. The method of claim 9, wherein the first or second type of laser operates in a region selected from at least one of an ultraviolet, a visible, and an infrared region.

12. The method of claim 1, wherein the first processing source includes a first laser operating at a first power and the second processing source includes a second laser operating at a second power, wherein the first power and the second power are not the same.

13. The method of claim 12, wherein the first or second laser power is in the range of about 10 to about 100 watts.

14. The method of claim 1, wherein the first processing source forms a single kerf and the second processing source forms a plurality of kerfs that does not include the single kerf.

15. The method of claim 1, further including the step of contacting the first conductive component with at least one chemical component.

16. The method of claim 15, wherein the at least one chemical component includes at least one compound selected from the group consisting of potassium ferricyanide, ruthenium hexamine, glucose oxidase and glucose dehydrogenase.

17. The method of claim 1, wherein at least one of the first conductive component, the second conductive component, and the third conductive component is formed from a semi-conductive material.

18. A method of manufacturing test strips, comprising:
    forming a reel containing a conductive layer and a base layer;
    forming a first kerf in the conductive layer, wherein the first kerf is formed using a first focused laser beam moved relative to the conductive layer along the first kerf;
    forming a second kerf in the conductive layer, wherein the second kerf is formed using a second focused laser beam moved relative to the conductive layer along the second kerf, the first laser beam being different to the second laser beam;
    separating one or more test strips from the reel using a singulation process.

19. The method of claim 18, wherein the singulation process includes at least one technique selected from the group consisting of laser ablation, stamping, cutting, and etching.

20. The method of claim 18, wherein the first laser beam has a first beam width and the second laser beam has a second beam width, wherein the first beam width and the second beam width are not the same.

21. The method of claim 20, wherein the first beam width is at least approximately 20 micro-meters.

22. The method of claim 20, wherein the second beam width is at least approximately 100 micro-meters.

23. The method of claim 18, wherein at least one laser beam removes substantially all conductive material between adjacent conductive components.

24. The method of claim 18, wherein the first laser beam is emitted from a first type of laser and the second laser beam is emitted from a second type of laser, wherein the first type of laser and the second type of laser are not the same.

25. The method of claim 24, wherein the first or second type of laser is selected from the group consisting of a solid-state laser, a copper vapor laser, a diode laser, a carbon dioxide laser, and an excimer laser.

26. The method of claim 24, wherein the first or second type of laser operates in a region selected from at least one of an ultraviolet, a visible, and an infrared region.

27. The method of claim 18, wherein the first laser beam is emitted from a first laser operating at a first power and the second laser beam is emitted from a second laser operating at a second power, wherein the first power and the second power are not the same.

28. The method of claim 27, wherein the first or second laser power is in the range of about 10 to about 100 watts.

29. The method of claim 18, further including the step of contacting at least part of the conductive layer with at least one chemical component.

30. The method of claim 29, wherein the at least one chemical component includes at least one compound selected from the group consisting of potassium ferricyanide, ruthenium hexamine, glucose oxidase and glucose dehydrogenase.

31. The method of claim 18, wherein at least one of the first conductive component, the second conductive component, and the third conductive component is formed from a semi-conductive material.

32. The method of claim 18, further including application of a spacer layer to the conductive layer or the base layer.

33. The method of claim 32, wherein the second kerf is formed after application of the spacer layer.

34. The method of claim 32, further including application of a cover to the spacer layer.

35. The method of claim 18, wherein the conductive layer is formed using a technique selected from the group consisting of direct writing, sputtering, screen printing, contract printing, and lamination.

36. The method of claim 18, further including the step of applying to the conductive layer at least one of a second conductive layer and a semi-conductive layer.

37. The method of claim 36, wherein the second kerf is formed after application of at least one of the second conductive layer and the semi-conductive layer.

* * * * *